United States Patent [19]

Barnard et al.

[11] Patent Number: 5,380,650
[45] Date of Patent: Jan. 10, 1995

[54] ENHANCED LUMINESCENT ASSAY

[75] Inventors: Geoffrey J. R. Barnard, Cheam, England; Dean Goodwin, Dyke, Va.; Robert S. Davidson, Leicester, England

[73] Assignee: British Technology Group Ltd., London, England

[21] Appl. No.: 340,413

[22] PCT Filed: Sep. 3, 1987

[86] PCT No.: PCT/GB87/00617
§ 371 Date: Mar. 23, 1989
§ 102(e) Date: Mar. 23, 1989

[87] PCT Pub. No.: WO88/01746
PCT Pub. Date: Mar. 10, 1988

[30] Foreign Application Priority Data

Sep. 3, 1986 [GB] United Kingdom ............... 8621261

[51] Int. Cl.$^6$ .................. C12M 1/28; C07C 13/00; C07C 205/05; C07D 471/00
[52] U.S. Cl. ............................. 435/28; 435/4; 435/968; 435/975; 435/7.1; 436/63; 436/172; 436/800; 436/809; 546/184; 546/112; 546/208; 546/226; 546/245; 546/273; 548/181; 548/204; 548/312.1; 548/314.7; 548/364.7; 548/451; 548/455; 544/129
[58] Field of Search ............. 435/28, 968, 975, 4, 435/7.1, 7.2; 436/63, 172, 800, 809, 506; 546/184, 112, 208, 226, 245, 273; 548/181, 204, 312.1, 314.7, 364.7, 451, 455, 495; 544/129

[56] References Cited

U.S. PATENT DOCUMENTS 4,842,997 6/1989 Carter .................................. 435/28

FOREIGN PATENT DOCUMENTS 87959A  9/1983 European Pat. Off. .
116454A 8/1984 European Pat. Off. .
118634A 9/1984 European Pat. Off. .
210449A 2/1987 European Pat. Off. .
219352A 4/1987 European Pat. Off. .
2162946A 2/1986 United Kingdom .

OTHER PUBLICATIONS

Johnson J Immunological Methods 55 (1982) pp. 231–242.
T. P. Whitehead et al., Clinical Chemistry 25, 1531–1546 (1979).
G. J. Barnard et al. in "Alternative Immunoassays" ed. W. P. Collins, John Wiley & sons Chichester, U.K. 1984, pp. 123–152.
W. Klingler et al., Trends in Analytical Chemistry 2, 132–136 (1983).
P. Bischof et al., Tetrahedron Letters 46, 4025–4028 (1969).
N. Duran et al., Cellulose Chemistry & Technology 18, 411–419 (1985).
K. Honda et al., Analytica Chimica Acta 177, 111–120 (1985).
A. Lundin & L. Hallander Poster displayed at the 4th International Symposium on Biolumiescence and Chemiluminescence held at Freiburg, W. Germany, 8–10 Sep. 1986.

Primary Examiner—William H. Beisner
Assistant Examiner—Jane Williams
Attorney, Agent, or Firm—Nixon & Vanderhye

[57] ABSTRACT

In an assay in which a ligand is labelled by conjugation to a dihydrophthalazinedione (DPD), e.g. luminol or isoluminol, and the conjugated DPD is reacted with an oxidant, e.g. hydrogen peroxide, and an active heme group catalyst, e.g. microperoxidase, the light intensity is enhanced by certain sterically hindered amines defined as saturated bicyclic compounds having a nitrogen atom at one or both bridgehead positions or a piperidine ring compound having four $C_{1-4}$ alkyl groups at the 2- and 6- positions. 1,4-Diazabicyclo[2.2.2]-octane, known as "DABCO" is preferred.

11 Claims, No Drawings

ENHANCED LUMINESCENT ASSAY

BACKGROUND OF THE INVENTION

1. Field of the Invention

The present invention relates to an enhanced luminescent assay, particularly immunoassay, and to a diagnostic kit for use in the assay. The luminescent assays with which the present invention is concerned are those depending on a chemiluminescent reaction (a chemical reaction that results in the emission of light). The luminescent emission is generally of sufficient duration to enable the light emitted to be detected or measured, and thereby to allow the detection or quantification of an analyte. The chemiluminescent reaction with which this invention is concerned is that between a 2,3-dihydro-1,4-phthalazinedione (DPD), especially luminol or isoluminol, with an oxidant, especially hydrogen peroxide, and a catalyst, especially peroxidase enzyme, which catalyses the oxidation of the DPD by the oxidant. The oxidation is accompanied by emission of light.

2. Description of the Prior Art

Luminescent assays making use of the above-mentioned peroxidase catalysed oxidation of a DPD can be of several major types, the commonest of which are those wherein horseradish peroxidase is conjugated to a ligand in order to label it and a luminescent reaction is used to detect or quantitate the label. The present invention relates exclusively to assays of a different kind, namely those wherein a chemiluminescent compound is used directly to label ligands such as proteins, hormones, haptens, steroids, nucleic acids, metabolites, antigens and/or antibodies. The chemiluminescent DPD such as luminol or isoluminol is normally conjugated to a ligand. Chemiluminescence can be detected by adding peroxidase and an oxidant to the reacted conjugate.

A review of luminescent assays has been published by T. P. Whitehead et. al., Clinical Chemistry 25, 1531–1546 (1979).

The sensitivity of the peroxidase-catalysed chemiluminescent oxidation of DPDs can be enhanced by including in the reagents an enhancer, namely a 6-hydroxybenzothiazole (European Patent 87959B of NRDC), a phenol selected from a narrowly defined class (European Patent 116454B or U.S. Pat. No. 4,598,044 assigned to NRDC) or an aromatic amine selected from a narrowly defined class (UK Patent Application 2162946A of NRDC or European Patent Publication 219352A (Minnesota Mining & Mfg. Co.).

In European Patent Application Publication 210449A (Molecular Diagnostics Inc.) it is alleged that ammonia and water-soluble organic amines are enhancers of chemiluminescent reactions. The amines specifically mentioned are aliphatic polyamines such as spermire, spermidine and butylenediamine, tertiary alkylamines, pyridine, azoles, thiazines, aryl amines and benzylamine. However, little evidence of enhancement is provided in that patent specification.

Despite these prior disclosures, none of which exemplifies enhancement of an assay using direct labelling of a ligand by a DPD, it has been a problem to find amines which enhance such an assay to a high level of light intensity and provide a significantly greater light intensity when the DPD conjugate is present than when it is absent.

SUMMARY OF THE INVENTION

It has now been found that certain saturated heterocyclic amines enhance the chemiluminescent oxidation of a DPD. These amines have the characteristic that they lose an electron easily to form positive ions. They are either tertiary amines or secondary amines in which the hydrogen atom attached to the nitrogen is well shielded or sterically hindered. More precisely, the amines of interest are saturated bicyclic compounds having a nitrogen atom at one or both bridgehead positions and piperidine ring compounds having four lower ($C_{1-4}$) alkyl groups at the 2- and 6- positions (the carbon atoms adjacent to the nitrogen). The invention provides a luminescent or luminometric assay which comprises carrying out a chemiluminescent reaction between a catalyst having an accessible heme group, preferably a peroxidase enzyme, most preferably microperoxidase, an oxidant, preferably hydrogen peroxide, and a chemiluminescent DPD conjugated to a ligand said ligand being a molecular residue relatable to a substance to be assayed, and detecting or measuring the chemiluminescence produced, characterized in that the reaction is carried out in the presence of such an amine as an enhancer. It includes also a kit for use in the assay comprising the said chemiluminescent DPD conjugate, peroxidase enzyme and amine enhancer.

DESCRIPTION OF THE PREFERRED EMBODIMENTS

The amine enhancers can contain ring substituents, or, in the case of the already substituted piperidines, further ring substituents, preferably lower ($C_{1-4}$) alkyl, hydroxy, chloro or bromo.

The currently preferred enhancer amines for use in the invention are:

| | | |
|---|---|---|
| 1,4-diazabicyclo[2.2.2]octane: ("DABCO" for short); this is the best enhancer. | 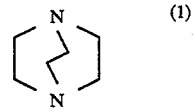 | (1) |
| Quinuclidine: | 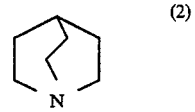 | (2) |
| 3-Quinuclidinol: | 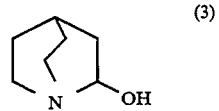 | (3) |
| 2,2,6,6-Tetramethylpiperidine and ring-substituted derivatives thereof, especially 4-substituted derivatives (where A represents a substituent, preferably 4-hydroxy) | 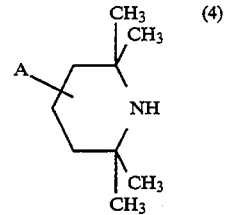 | (4) |

It is of interest that several other hindered amines, not within the scope of this invention, do not provide a good enhancement. For instance, 1,2-bismorpholinoethane gives a high intensity of luminescence whether a DPD is present or not and the difference (enhancement)

is relatively low. On the other hand, 1,6-bis-piperidinohexane and hexamethylenetetramine gave low intensity luminescence with moderate enhancement.

The concentration of DPD, oxidant, peroxidase and enhancer and also the reaction temperature and pH are all variables which can affect the intensity of luminescence and degree of enhancement and some adjustment will be required to obtain optimal results. The luminescence signal will also depend on the time for which the reagents are incubated and the method of measurement of luminescence.

The greater the excess of oxidant and catalyst relative to DPD, the quicker the light will develop to maximum intensity. In general, a molar excess of from $10^2$ to $10^6$ of each will usually be appropriate, but lower concentrations could be used where a long output of relatively low intensity is considered tolerable.

The invention is applicable to any of the assays described above or in the UK specification 2162946A, but especially to those in which the DPD is the direct label. In such assays the DPD label takes the place of a radiolabel or enzyme in conventional assays. Such DPD-labelled assays are well known, see e.g. G. J. Barnard et. al., in "Alternative Immunoassays", ed. W. P. Collins, John Wiley & Sons, Chichester UK, 1984, pages 123–152. It is then necessary to bond the DPD, preferably luminol or isoluminol, covalently to a ligand, such as a hapten antigen or antibody which is relatable in some way to the substance to be assayed. It can be the same as or behave comparably with the substance to be assayed or can be a binding partner thereof. Alternatively, it can be related more indirectly to the substance to be assayed, e.g. be the product of a reaction which is first undergone by that substance.

Generally stated, the kinds of assay known in ELISA technology are applicable to the present invention. These include predominantly sandwich, competitive and displacement assays. The invention is particularly useful for the competitive and displacement assay of haptens such as steroids. In the usual kind of competitive or displacement assay, the DPD-ligand conjugate competes with the analyte (containing a substance to be assayed of similar or the same structure as the ligand) for a limited number of binding sites on an antibody. The degree of competition depends of the relative affinities of the conjugate and analyte for the antibody as well as on their concentrations. The concentration of conjugate can be adjusted in the same manner as for an ELISA but will typically be from 0.001y to 1000y where y is the maximum expected concentration of analyte, preferably 0.02y to 0.5y.

Any of the known methods of conjugating the DPD label to such molecules can be used. By way of example, two conjugates used in the Examples herein are estradiol/isoluminol and estrone-3-glucuronide/isoluminol of formulae (5) and (6) respectively:

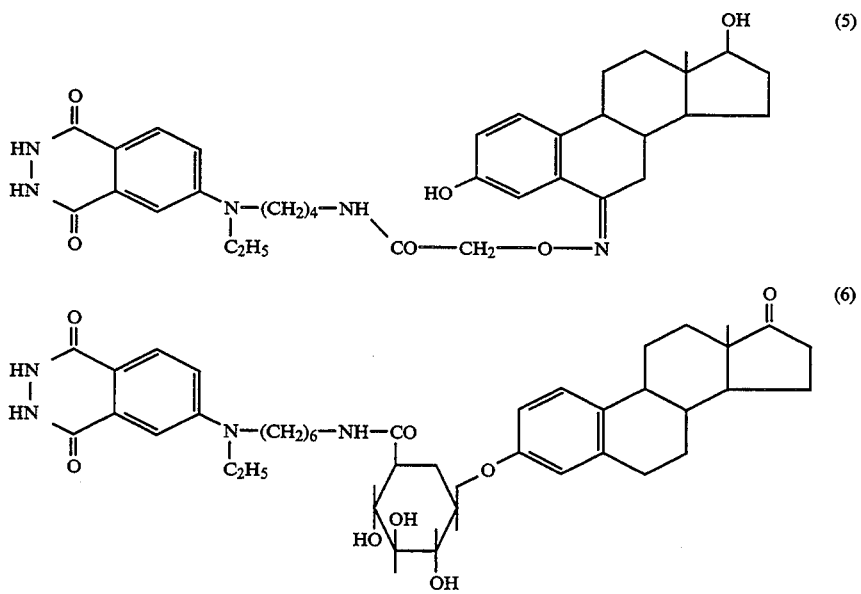

Preferred DPDs are those so described in UK Specification 2162946A, although it will be appreciated that they should be provided with a group to which a bridging arm can be attached for conjugation to a hapten etc. if the DPD is to be used for direct labelling. Luminol and isoluminol, which are preferred, possess an amine group as a ring substituent, whereby a bridging arm can be attached as in formula (7):

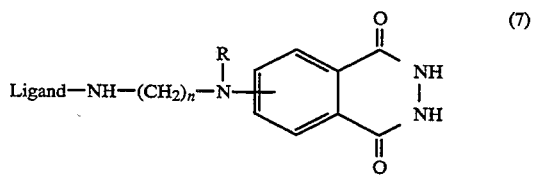

where R is a non-interfering organic group, preferably $C_{1-4}$ alkyl and n is 2 to 6, preferably 4 to 6. The remote amine group of the DPD can thus be linked through an amide linkage to a carbonyl group present in or introduced into the ligand such as a steroid. Isoluminol is preferred to luminol.

The preferred oxidant is hydrogen peroxide, but any added oxidant known to participate in the chemiluminescent reaction to be enhanced can be used. An example is t-butyl-hydroperoxide. Perborate ions can also be used. On the other hand oxidants known to be ineffective or poorly effective in chemiluminescent DPD reactions, such as potassium persulphate, are, of course, to be avoided.

The catalyst is preferably a peroxidase enzyme, most preferably microperoxidase. Other haem-containing molecules, for example haematin or haemoglobin, could be substituted for a peroxidase.

The luminescent reaction is carried out on the product of the assay steps. For example, in the conventional heterogenous format, the support material, to which the label becomes attached as a result of antigen-antibody binding, is washed to remove residual label present in solution. The label, in this case the DPD, is then detected or quantitated by initiating the luminescent reaction. The reactants can be added in any order, but it is preferred to minimize possible stray reactions by adding the oxidant or catalyst last.

The luminescent reaction can be conducted in an aqueous medium at any pH from neutral (pH7) to strongly alkaline (pH 13.8), but since some DPDs appear to decompose at very high pH, it is often best not to exceed 12.5. A pH of 9 or more gives the best results, especially one in the range 9 to 10.5.

The luminescent reaction works well at all ambient room temperatures in the range 15° to 30° C. It is a particular advantage of the invention that it is not necessary to cleave the DPD from the ligand to which it is conjugated in order to produce a sufficient intensity of light. The prior art practice of heating to about 60° C. can thus be dispensed with.

The major use of the present assay will be in clinical laboratories. It is usual for such laboratories to obtain the materials to be used in a given assay procedure in the form of an assay kit. In addition to the DPD conjugate, amine enhancer and catalyst, the kit may also contain an oxidant, but in many cases this material may be provided separately.

Preferably the catalyst, the oxidant, the enhancer and the chemiluminescent DPD will each be one of those substances mentioned above as preferred for use in the present assay. In the present assay kit the chemiluminescent DPD is conjugated to an appropriate ligand, e.g. to an antibody to the substance to be assayed. Preferably the kit comprises the conjugate of a DPD with a hapten, antigen or antibody, the catalyst for the oxidation of the DPD and the amine enhancer, each in a separate container.

Optionally the assay kit may also contain one or more standard solutions each containing a known amount of the substance to be assayed, and/or one or more of the preferred buffer solutions and/or the oxidant. Conveniently the assay kit may also include a reaction vessel suitable for use in conjunction with the apparatus used for the determination of the light emitted in the course of carrying out the assay. Also a mixing device may be included in the assay kit, for use in ensuring adequate admixture of the reagents.

The following Examples illustrate the invention.

EXAMPLE 1

In the following experiments the chemiluminescence of an estradiol-isoluminol conjugate of formula (5) was measured. These experiments are representative of the use of the isoluminol to label estradiol and then to perform a competitive or displacement assay in which free estradiol in a sample of a body fluid of a patient and labelled estradiol compete for a limited amount of insolubilised antiestradiol and the amount of label bound to the solid phase is measured. The amount of free estradiol in the sample is inversely proportional to the amount of label measured on the solid phase.

The experiments were performed by making up a mixture of the following solutions in double distilled water.

| | |
|---|---|
| Estradiol-isoluminol conjugate (1 ng/ml) | 100 μl |
| Microperoxidase from Sigma Chemical Co. Ltd., Poole, Dorset, UK (20 micrograms/ml) | 100 μl |
| Hydrogen peroxide (0.3% w/v, i.e. 3 mg/ml) | 100 μl |
| The additive being tested as an enhancer 25 mg/ml): | 100 μl |

The microperoxidase was added last, to the mixture of the other components in assay tubes. The pH of the mixture was measured. It was not significantly affected by the absence of the conjugate. Luminescence was read on an LKB-Nallac 1250 luminometer. No incubation time was allowed and the intensity of luminescence at maximum peak height was recorded. The results are shown in Table 1.

In order to compare the effect of the luminol label, conjunction with the additive tested as an enhancer, a series of "background" runs were performed. In these runs the conjugate was omitted, the components being the peroxidase, hydrogen peroxide and amine enhancer, made up to 400 ml. Comparison of the "signal with enhancer" runs, in which the conjugate, peroxidase, hydrogen peroxide and enhancer (100 microliters of each) were all present, with the "background" runs shows the utility of the assay.

In other runs, when the enhancer was replaced by 100 μl of double distilled water, the signal was very low, viz 2.93. (the signal without the enhancer can be improved by allowing the reactants to incubate before measuring the luminescence, but the delay involved in incubation is not always desirable).

It will be seen that all the amines tested gave good enhancement.

The signal without the enhancer can be improved by allowing the reactants to incubate before measuring the luminescence, but the delay involved in incubation is not always desirable.

TABLE 1

Effect of amine additive upon the chemiluminescence from a estradiol-isoluminol conjugate (without incubation of conjugate)

| Amine Enhancer (E) | Background (MP/ $H_2O_2$/E) | Signal with enhancer (MP/IL/$H_2O_2$/E) | pH of mixture |
|---|---|---|---|
| DABCO | 34.97 | 65.83 | 10.7 |
| QUINUCLIDINOL | 9.96 | 34.83 | 11.6 |
| 4-HYDROXY-2,2,6,6-TETRAMETHYL-PIPERIDINE | 2.37 | 22.49 | 11.1 |
| QUINUCLIDINE | 5.87 | 22.01 | 12.6 |
| 4-AMINO-2,2,6,6-TETRA METHYL-PIPERIDINE | 16.96 | 19.40 | 12.7 |

EXAMPLE 2

This Example illustrates enhancement of a reaction between free luminol, microperoxidase and hydrogen peroxide by DABCO. It is representative, inter alia, of a similar assay to that of Example 1, bearing in mind that free luminol and conjugated luminol are known to behave similarly (with quantitative differences) in their ability to participate in chemiluminescent reactions.

Solutions of volume 400 μl were prepared using specially distilled water. The concentrations and volumes of reagents used were:

| | | |
|---|---|---|
| Microperoxidase | 20 micrograms/ml | 100 microliters |
| DABCO | 50 or 25 mg/ml | 100 microliters |
| $H_2O_2$ | 0.3% w/v | 100 microliters |
| Luminol | various concentrations | 100 microliters |

Light emission from the $H_2O_2$/microperoxidase and $10^{-3}$, $10^{-9}$ and $10^{-11}$ dilutions of a 1 mg/ml luminol solution was determined in the presence and absence of DABCO. Typical results using 50 mg/ml DABCO are shown below in Table 2. Addition of DABCO raised the pH by 3.1 to 10.8, 10.7 and 10.6 respectively.

TABLE 2

| | Light emission (counts/60s) | | |
|---|---|---|---|
| Luminol Dilution | Signal without enhancer (MP/L/$H_2O_2$) | Signal with enhancer (MP/L/$H_2O_2$/DABCO) | Background (MP/$H_2O_2$/DABCO) |
| $10^{-3}$ | 147,472,221 | 835,562,582 | 52,711,222 |
| $10^{-9}$ | 815,299 | 71,869,754 | 28,912,109 |
| $10^{-11}$ | 988,000 | 24,958,506 | 28,706,174 |

It was concluded as follows:
1) DABCO-enhanced light emission from the microperoxidase/luminol/$H_2O_2$ reaction (5 to more than 75-fold).
2) DABCO slightly increased (more than 20-fold) light emission from the microperoxidase/$H_2O_2$ reaction in the absence of luminol.
3) The kinetics of light emission from the DABCO-enhanced MP/luminol/$H_2O_2$ reaction were rapid and flash-like, but with a slight delay after initiation.
4) DABCO appeared to react with luminol in a synergistic manner.

EXAMPLE 3

This Example illustrates an assay for determining urinary estrone-3-glucuronide ($E_1$-3-G), which is a metabolite of estradiol. This assay is useful for measuring follicular development in women in order to predict the time of ovulation, which is essential to successful in vitro fertilization treatment. A double-antibody solid phase competitive immunoassay was used. The second antibody, donkey anti-rabbit IgG was absorbed to the walls of polystyrene tubes. Isoluminol labelled conjugate ($E_1$-3-G-aminohexyl-ethyl-isoluminol) and a primary antibody (rabbit anti-$E_1$-3-G-BSA) were incubated with a urine sample. After removal of the liquid phase and thorough washing of the tubes, the amount of isoluminol bound to the tubes was assayed by adding a sodium hydroxide solution of DABCO and microperoxidase and measuring the chemiluminescence produced.

REAGENTS

Authentic $E_1$-3-G was kindly donated by Dr. W. Coulson of the Courtauld Institute of Biochemistry, The Middlesex Hospital Medical School, London. DABCO, microperoxidase (MP11), bovine serum albumin (BSA Fraction V) and Sepharose-Protein A were purchased from Sigma Chemical Co. Ltd., Poole, Dorset, U.K. A polyclonal antiserum (rabbit) to $E_1$-3-G-6-bovine serum albumin was kindly donated by Dr. W. Butt of the Birmingham Hospital for Women, Birmingham, U.K. An IgG fraction of donkey anti-rabbit antiserum was prepared by affinity chromatography on Protein-A Sepharose CL-4B. All other reagents were obtained from BDH (London) Ltd., Baird Road, Enfield, London, U.K.

The assay buffer was 0.1M phosphate buffer: 2.5 g sodium dihydrogen orthophosphate.$2H_2O$ plus 11.9 g disodium hydrogen orthophosphate dissolved in one liter of double distilled water containing 0.1% gelatin and 0.9% sodium chloride (pH 7.4). Microperoxidase was dissolved in phosphate buffer and the stock solution (1 mg/ml) was stored at 4° C. The working solution was 20 micrograms/ml (1:50, v/v). In addition, a barbital buffer was prepared: 14.4 g sodium barbital dissolved in one liter of double distilled water containing 0.1% BSA and 0.9% sodium chloride (pH 8.6). The oxidant solution was prepared by adding 100 microliters of 30% w/v hydrogen peroxide solution to 10 ml of doubly distilled water.

Preparation of Chemiluminescent Label Conjugate

6-[N-4-aminohexyl)-N-ethyl]amino-2,3-dihydrophthalazine-1,4-dione (AHEI) of formula (7) was synthesized according to a method previously reported. The conjugation of AHEI to $E_1$-3-G and the purification of the product was similar to the methods described for estriol-16-alpha-glucuronide-ABEI conjugate by F. Kohen et. al., Steroids 36, 405–419 (1980).

Sample Collection and Dilution

Samples of total urine produced over 24 hours were collected daily from healthy, non-pregnant female volunteers throughout their complete menstrual cycle. The total volume of urine was recorded for each day's collection.

Antibody-Coated Tubes

Donkey anti-rabbit IgG was suitably diluted (in excess) in the coating buffer. 300 microliters were added to each polystyrene assay tube (Lumacuvette, Laboratory Impex Ltd.,) Impex House, Lion Road, Twickenham, Middlesex TW1 4JF, U.K.). After an overnight incubation at 4° C., the coating buffer was aspirated to waste and 400 microliters of assay buffer were added to each tube. After incubation for 30 min at 22° C. the tubes were stored at 4° C. until required. When stored under these conditions the coated tubes remained completely stable for several months.

Immunoassay Procedure 20 microliters of urine or 20 microliters of standard (range 0 to 1120 nmol/l of assay buffer) were added in duplicate to the second antibody-coated tubes. 200 microliters of $E_1$-3-G-AHEI (1 ng; approximately 100,000 counts/10 sec.) and 100 microliters of suitably diluted polyclonal anti-$E_1$-3-G antiserum (1:10,000 v/v) were added and the mixture was incubated at 22° C. for 30 mins. Subsequently, the contents of the tube were removed by aspiration. 500 microliters of assay buffer were added to each tube and subsequently removed by aspiration. This washing step was repeated twice.

To each tube in turn, 200 microliters of 0.2M sodium hydroxide containing DABCO at a concentration of 25 g/liter were added followed by the addition of 100 microliters of dilute microperoxidase. The pH of the final mixture was 13.1. The tube was then placed in the luminometer (Biolumat; Laboratory Impex Ltd.,) The chemiluminescence reaction was initiated by the rapid injection of 100 microliters of the 0.3% w/v hydrogen peroxide solution by an automatic dispenser. The signal was integrated for 10 secs after the addition of the peroxide and the value recorded.

The results shown in Table 3 are those obtained to establish a calibration curve for the assay. Eight concentrations of $E_1$-3-G were employed.

TABLE 3

Calibration of assay for estrone-3-glucuronide

| Conc of $E_1$-3-G standard solution, nanomoles/liter | Counts, mV/S. (mean of two experiments) |
|---|---|
| 0 | 67098 |
| 35 | 57699 |
| 70 | 47458 |
| 140 | 38820 |
| 280 | 29768 |
| 560 | 23970 |
| 1120 | 18344 |
| 2240 | 15132 |

EXAMPLE 4

This Example illustrates another assay for estrone-3-glucuronide ($E_1$-3-G) in which the luminescent reaction was carried out at different pHs and compared with the conventional isoluminol label assay in which the reagents are incubated at 60° C. for 1 hour to cleave the label before the luminescence is measured.

Reagents

The reagents used were as in Example 3 except that a monoclonal antibody to $E_1$-3-G was used in place of the polyclonal antibodies.

The coating buffer used to attach anti-$E_1$-3-G to the polystyrene tubes was 0.1M carbonate buffer, pH 10. The assay buffer was phosphate buffered saline with 1 g./liter of gelatin (PBSG) (0.1M, pH7.4). Microperoxidase (MP-11) was dissolved in 0.05M phosphate buffer to make a stock solution of 1 mg/ml PBS. A working solution of 2.6 μM enzyme (a 1:50 dilution) was used in the assay. The oxidant, hydrogen peroxide, was 0.3% w/v (100 μl).

Methods

The monoclonal antiserum to $E_1$-3-G (1 mg/ml) was diluted by 500 fold in coating buffer and 300 μl removed and added to each tube. After an overnight incubation at 4° C. each tube was aspirated and 400 μl of assay buffer (0.1M, pH 7.4), PBSG, added. These tubes were again aspirated after a 30 minute incubation at room temperature.

Standards of $E_1$-3-G ranging from 40 ng/ml PBSG to 0 ng/ml PBSG were prepared. The stock solution of $E_1$-3-G-AHEI at a concentration of 100 ng/ml was diluted one hundred fold in PBSG. A competitive assay was initiated by adding 100 μof the diluted $E_1$-3-G-AHEI and 100 μl of $E_1$-3-G standards of various concentrations to the coated tubes. This mixture was incubated at room temperature for 1 hour, after which the tubes were aspirated and washed three times with double distilled water.

At this point 100 μl of a 10 mg/ml solution of DABCO in NaOH at one of three different molarities was added, with microperoxidase, to each tube and chemiluminescence initiated by the addition of 100 μl of hydrogen peroxide.

For comparative purposes an experiment was carried out in which sodium hydroxide (2M) replaced DABCO. After the tubes were washed, sodium hydroxide, (300 μl) was added and the tubes incubated for a further hour at 60° C. When the tubes had cooled to room temperature, microperoxidase and hydrogen peroxide were added as before. The light was measured in the same luminometer as in Example 3 and the light signal produced was integrated for 10 seconds.

The results are shown in Table 4 below. It will be seen that at the 2M concentration of sodium hydroxide, the difference in signal between the 40 ng/ml and 0 standards is about 32,000 mV/S, which is nearly as much as the 37,000 mV/S difference by the prior method involving heating at 60° C.

TABLE 4

| Conc. of $E_1$-3-G standard in PBSG | Light intensity mV/Sec. DABCO (10 mg/ml) in | | | Comparative (no DABCO, Δ 60° C., 2M NaOH pH 13.7) |
|---|---|---|---|---|
| | 0.2M NaOH (pH 11.8) | 0.5M NaOH (pH 12.8) | 2M NaOH (pH 13.6) | |
| 40 ng/ml | 10,275 | 16,865 | 12,770 | 8,930 |
| 20 ng/ml | 12,030 | 20,745 | 16,300 | 9,775 |
| 10 ng/ml | 14,600 | 24,715 | 18,685 | 15,135 |
| 5 ng/ml | 15,795 | 25,205 | 29,385 | 22,260 |
| 2.5 ng/ml | 17,430 | 26,590 | 36,045 | 32,050 |
| 1.25 ng/ml | 20,425 | 32,735 | 42,930 | 39,015 |
| 0 ng/ml | 22,370 | 36,880 | 44,850 | 46,190 |
| NSB* ng/ml | 4,390 | 4,290 | 10,595 | 2,630 |

NSB (Non-Specific Binding) was obtained from the uncoated tube + $E_1$-3-G-AHEI (100 μl) + 40 ng/ml $E_1$-3-G (100 μl).

EXAMPLE 5

The procedure of Example 4 was repeated except that 100 μl of a 1 mg/ml 0.2M NaOH solution of haematin diluted 1:50 in double distilled water was substituted for microperoxidase and DABCO solutions of concentration 10 mg and 20 mg/ml were used.

Haematin produced a good enhancement, the light count for zero $E_1$-3-G rising from 7,090 to 69,970 mV/S. and for 40 ng/ml $E_1$-3-G from 7,380 to 38,520 mV/S.

Good calibration curves were obtained using haematin as the catalyst. Abbreviated results are shown in Table 5. The prior art method without DABCO and incubating the tubes for 1 hour at 60° C. in 2M NaOH failed to give a calibration curve, possibly because haematin is too sensitive a catalyst for use when the isoluminol label is cleaved from the AHEI.

TABLE 5

| Conc. of $E_2$-3-G standard in PBSG | Light intensity mV/Sec. | | |
|---|---|---|---|
| | DABCO (20 mg/ml) in 0.5M NaOH (pH 13.1) | DABCO (10 mg/ml) in 0.5M NaOH (pH 13.1) | DABCO (20 mg/ml) in 1M NaOH (pH 13.6) |
| 40 ng/ml. | 38,520 | 24,855 | 32,965 |
| 20 ng/ml. | 42,760 | 29,670 | 38,360 |
| 10 ng/ml. | 47,525 | 35,225 | 40,500 |
| 5 ng/ml. | 52,715 | 39.975 | 44,365 |
| 2.5 ng/ml. | 58,270 | 44,210 | 54,890 |
| 1.25 ng/ml. | 63,445 | 49,115 | 64,475 |
| 0 ng/ml. | 69,970 | 53,225 | 74,490 |
| NSB* ng/ml. | 20,310 | 14,300 | 32,019 |

*NSB (Non-Specific Binding) was obtained as noted in Table 4.

We claim:

1. In a luminescent or luminometric assay which comprises carrying out a chemiluminescent reaction between a catalyst having an accessible heme group, an oxidant and a chemiluminescent dihydrophthalazinedione (DPD) conjugated to a molecular residue relatable to a substance to be assayed, and detecting or measuring the chemiluminescence produced, the improvement wherein said reaction is carried out in the presence of an enhancer comprising a saturated bridged bicyclic compound having a nitrogen atom at one or both bridgehead positions or a piperidine ring compound having four $C_{1-4}$ alkyl groups at the 2- and 6- positions.

2. An assay according to claim 1 wherein the DPD is isoluminol or luminol.

3. An assay according to claim 1 wherein the enhancer is 1,4-diazabicyclo [2.2.2] octane.

4. An assay according to claim 1 wherein the catalyst is microperoxidase.

5. An assay according to claim 1 wherein a competitive assay is carried out for a hapten in aqueous solution, whereby the DPD-conjugate becomes bound to a support, the support is washed, the oxidant, catalyst and enhancer are added and the luminescence is detected or measured at ambient temperature and at pH 9 to 10.5.

6. An assay kit for carrying out a luminescent or luminometric assay, comprising in separate containers:
(1) a catalyst having an accessible heme group,
(2) an oxidant,
(3) a chemiluminescent dihydrophthalazinedione (DPD) conjugated to a molecular residue and
(4) an enhancer comprising a saturated bridged bicyclic compound having a nitrogen atom at one or both bridgehead positions or a piperidine ring compound having four $C_{1-4}$ alkyl groups at the 2- and 6- positions.

7. A kit according to claim 6 wherein the DPD is isoluminol or luminol.

8. A kit according to claim 6 wherein the catalyst is microperoxidase.

9. A kit according to claim 6 wherein the DPD is conjugated to a hapten.

10. An assay according to claim 1 wherein the DPD is isoluminol or luminol, the enhancer is 1,4-diazabicyclo [2.2.2] octane, the catalyst is microperoxidase and the DPD is conjugated to a hapten, antigen or antibody.

11. A kit according to claim 6 wherein the DPD is isoluminol or luminol, the enhancer is 1,4-diazabicyclo [2.2.2] octane, the catalyst is microperoxidase and the DPD is conjugated to a hapten, antigen or antibody.

* * * * *